United States Patent
Sugiyama et al.

(10) Patent No.: US 8,301,225 B2
(45) Date of Patent: Oct. 30, 2012

(54) MAGNETIC RESONANCE IMAGING APPARATUS, IMAGE PROCESSING APPARATUS, AND IMAGE PROCESSING METHOD

(75) Inventors: Atsuko Sugiyama, Nasushiobara (JP); Hitoshi Yamagata, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 201 days.

(21) Appl. No.: 12/833,477

(22) Filed: Jul. 9, 2010

(65) Prior Publication Data
US 2011/0009732 A1    Jan. 13, 2011

(30) Foreign Application Priority Data

Jul. 10, 2009 (JP) ................................ 2009-164084
Jun. 18, 2010 (JP) ................................ 2010-139868

(51) Int. Cl.
*A61B 5/055* (2006.01)
*G01V 3/00* (2006.01)
(52) U.S. Cl. ...................................... 600/410; 324/309
(58) Field of Classification Search .................. 600/407, 600/410; 324/306
See application file for complete search history.

(56) References Cited

U.S. PATENT DOCUMENTS
5,771,893 A    6/1998    Kassai et al.

OTHER PUBLICATIONS

Japan Industries Association of Radiological Systems, published by Nago Bijutsu Insatsu Kabushiki Kaisha, "iyou Gazou Houshasan Kiki Handbook", (2001), pp. 176-177, with translation: 3.6.4 (f MRK: functional MRI).

*Primary Examiner* — Michael Rozanski
(74) *Attorney, Agent, or Firm* — Nixon & Vanderhye PC (57) ABSTRACT

A functional image generating unit that generates a functional image from a magnetic resonance image generated by collecting a magnetic resonance signal from a subject who executes a task with an intermission of a resting period. An image generation controlling unit controls the functional image generating unit so that a plurality of functional images along a time series are generated by separating a plurality of magnetic resonance images generated along the time series during a collecting period (in which the resting period and a task-execution period are repeated a plurality of times along the time series) into image groups, each corresponding to a predetermined temporal phase. A statistical process is performed on each of the image groups and a display controlling unit exercises control so that the functional images are displayed by a display unit.

19 Claims, 9 Drawing Sheets

EACH GROUP MADE UP OF FOUR PHASES IS SET AS STATISTIC PROCESS BLOCK

FIG.9A

EACH GROUP MADE UP OF TWO BLOCKS IS SET AS STATISTIC PROCESS BLOCK

FIG.9B

⟷ STATISTIC PROCESS BLOCKS

MAGNETIC RESONANCE IMAGING APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2009-164084, filed on Jul. 10, 2009, and Japanese Patent Application No. 2010-139868, filed on Jun. 18, 2010; the entire contents of all of which are incorporated herein by reference.

FIELD

Embodiments described herein relate generally to a magnetic resonance imaging apparatus, an image processing apparatus, and an image processing method.

BACKGROUND

Conventionally, Magnetic Resonance Imaging (MRI) apparatuses have popularly been used not only for morphological image diagnosis, but also for functional image diagnosis. More specifically, an MRI apparatus is capable of providing an fMRI image in which brain activities are expressed by using a method called "functional Magnetic Resonance Imaging (fMRI)" (see, for example, "Iyou Gazou Houshasen Kiki Handbook" edited by the Japan. Industries Association of Radiological Systems and published by Nago Bijutsu Insatsu Kabushiki Kaisha, 2001, pages 176-177).

The fMRI method is a method for generating the fMRI image in which activated areas of the brain are expressed by utilizing a Blood Oxygenation Level Dependent (BOLD) effect.

Next, the BOLD effect will be explained. In an activated area of the brain that has been activated by a movement or a stimulus, the blood flow rate increases, and also, because oxygen is supplied from the capillaries in the activated area to nerve cells, hemoglobin combined with oxygen (i.e., oxidized hemoglobin) is reduced so as to become reduced hemoglobin. In this situation, the degree with which the oxygen consumption amount of the nerve cells increases is lower than the degree with which the blood flow rate increases. As a result, the amount of oxidized hemoglobin in the venous blood within the activated area increases in a relative manner. In addition, oxidized hemoglobin is more difficult to be magnetized than reduced hemoglobin. In other words, the BOLD effect refers to a phenomenon where "in an activated area of the brain, the magnetic susceptibility decreases so that the intensity of the magnetic resonance signal changes".

Accordingly, it is possible to specify a brain function activated site by generating a Magnetic Resonance Image (MRI) while an examined subject continuously and repeatedly performs a task for activating the motor area, the visual area, the auditory area, the language area, the sensory cortex, and the like, with intermissions of resting periods each called a "rest" and by comparing images corresponding to task periods with images corresponding to rest periods. In addition, by comparing images that have been taken, for example, while tasks that have mutually-different contents are being executed, it is possible to specify a site that is activated during all the mutually-different tasks in common with one another and to specify a site that is peculiarly activated during each of the mutually-different tasks.

An example of an image analyzing process to specify a brain function activated site can be explained as follows: First, an average image of all the images during the rest periods and an average image of all, the images during the task periods are obtained. Subsequently, a "t-test" is performed for determining a statistically significant difference based on a difference value and a standard error between the two population mean values with respect to the two average images, so that a "t-value image" is generated as an fMRI original image. Further, a linear correlation coefficient is calculated, and also, a correlation coefficient between pixel values of the fMRI original image and a reference function is calculated, so that a correlation coefficient image is generated as an fMRI image.

Figure 11:
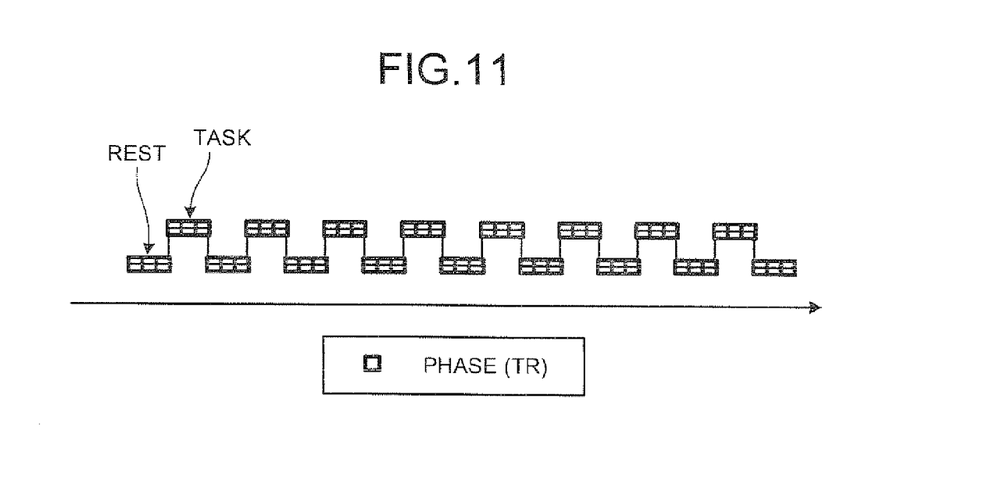
FIG. 11 is a drawing for explaining a block setting.

In this situation, a setting for the lengths of the time periods during which the rests and the tasks are executed is designed with blocks that are arranged with predetermined intervals. More specifically, as shown in FIG. 11, the setting for the lengths of the time periods during which the rests and the tasks are executed is expressed with a designed formation in which model blocks including rest-period blocks for having a rest and the task-period blocks for activating the brain are arranged along the time series. Thus, the setting is called a "block setting". FIG. 11 is a drawing for explaining an example of the block setting.

A block setting process is performed by an operator who is a medical doctor or the like by inputting, as parameters, numerical values such as the quantity of rest-period blocks and task-period blocks and the number of times the rests and the tasks are repeatedly executed, together with the type of the task. For example, the parameters are input by using, as shown in FIG. 11, temporal phases (hereinafter, "phases") that are expressed by using a repetition time (hereinafter, a "TR") as a unit. Further, the block setting is used during an image analyzing process, which is performed after the images during the rest periods and the task periods have been collected.

In the current circumstances, there are often situations in which it takes a certain period of time for the brain to be activated after being stimulated, depending on the stimulus applied to the examined subject.

According to the conventional technique described above, however, the fMRI image is generated by using the data that has been collected during all the task periods and all the rest periods, while excluding the data obtained immediately after the collecting process is started. As a result, a problem remains where, even by referring to the fMRI image, it is not possible to understand, from the image, the manner in which the brain function activated site changes over the course of time.

BRIEF DESCRIPTION OF THE DRAWINGS

FIGS. 8A and 83 are drawings for explaining a first modification example;

DETAILED DESCRIPTION

In one embodiment, a magnetic resonance imaging apparatus includes a functional image generating unit, an image generation controlling unit and a display controlling unit. The functional image generating unit generates a functional image, which is a functional-diagnosis-purpose magnetic resonance image, from a magnetic resonance image that has been generated by collecting a magnetic resonance signal from an examined subject who executes a task with an intermission of a resting period. The image generation controlling unit controls the functional image generating unit so that the functional image generating unit generates a plurality of functional images along a time series by separating a plurality of magnetic resonance images that have been generated along the time series during a collecting period into image groups each of which corresponds to a predetermined temporal phase and by performing a statistic process on each of the image groups resulting from the separation, the collecting period being configured so that the resting period and a task-execution period during which the task is executed are repeated therein a plurality of times along the time series. The display controlling unit exercises control so that the plurality of functional images along the time series that have been generated under control of the image generation controlling unit are displayed by a predetermined display unit.

Exemplary embodiments of a magnetic resonance imaging apparatus will be explained in detail, with reference to the accompanying drawings. Hereinafter, a magnetic resonance imaging apparatus will be referred to as an "MRI apparatus". Also, in the following sections, examples in which brain-function-diagnosis-purpose magnetic resonance images (i.e., fMRI images) of a patient are taken by an MRI apparatus will be explained.

Figure 1:
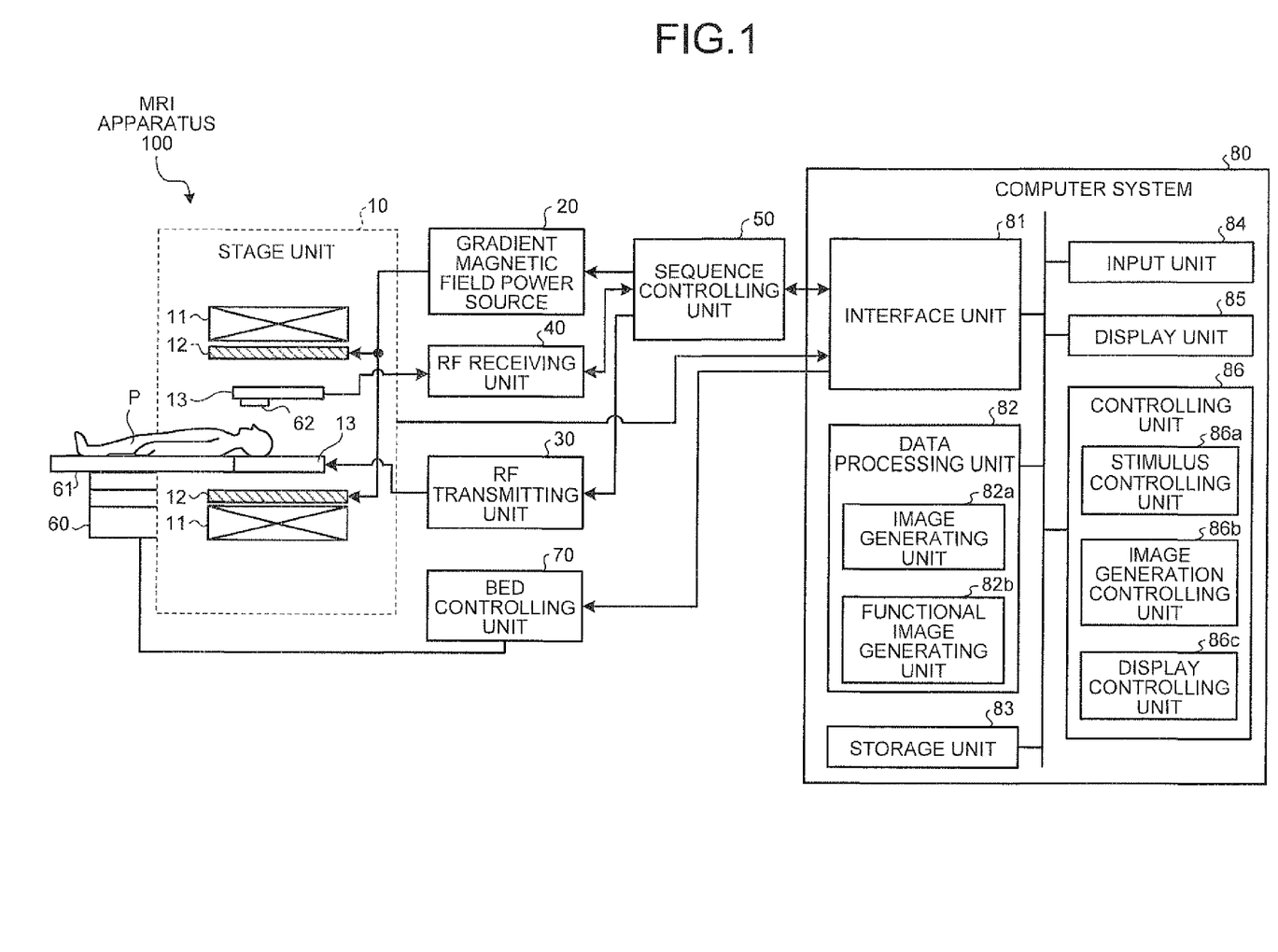
FIG. 1 is a drawing for explaining a configuration of an MRI apparatus according to an embodiment.

First, a configuration of an MRI apparatus according to an embodiment will be explained. FIG. 1 is a drawing for explaining the configuration of the MRI apparatus according to the embodiment. As shown in FIG. 1, an MRI apparatus 100 according to the present embodiment includes: a stage unit 10; a gradient magnetic field power source 20; a radio frequency (RE) transmitting unit 30; an RE receiving unit 40; a sequence controlling unit 50; a bed unit 60; a bed controlling unit 70; and a computer system 80.

The stage unit 10 is a device configured so as to radiate a high-frequency magnetic field onto a patient P who is placed in a magnetostatic field and to detect a magnetic resonance signal that is thereby released from the patient P. The stage unit 10 includes a magnetostatic field magnet 11, a gradient magnetic field coil 12, and a transmission/reception Radio Frequency (RE) coil 13.

The magnetostatic field magnet 11 is a superconductive magnet that is formed in the shape of, for example, a hollow circular cylinder and that generates a uniform magnetostatic field in the space on the inside thereof. The magnetostatic field magnet 11 may be a superconductive magnet that is included in an open-type MRI apparatus and generates a uniform magnetostatic field.

The gradient magnetic field coil 12 is a coil that is formed in the shape of a hollow circular cylinder and is disposed on the inside of the magnetostatic field magnet 11. The gradient magnetic field coil 12 is structured by combining three coils that respectively correspond to X-, Y-, and Z-axes that are orthogonal to one another. According to the present embodiment, each of the three coils generates, on the corresponding one of the X-, Y-, and Z-axes, a gradient magnetic field configured in such a manner that the magnetic field in the Z-axis direction linearly changes with respect to the distance from the center of the gradient magnetic field, by individually receiving a supply of electric current from the gradient magnetic field power source 20 (explained later).

Further, the gradient magnetic fields on the X-, Y-, and Z-axes that are generated by the gradient magnetic field coil 12 correspond to, for example, a slice selecting gradient magnetic field Gs, a phase encode gradient magnetic field Ge, and a read-out gradient magnetic field Gr, respectively. The slice selecting gradient magnetic field Gs is used for arbitrarily specifying an image-taking cross-sectional plane. The phase encode gradient magnetic field Ge is used for changing the phase of the magnetic resonance signal according to a spatial position. The read-out gradient magnetic field Gr is used for changing the frequency of the magnetic resonance signal according to a spatial position.

As shown in FIG. 1, the transmission/reception RF coil 13 is disposed on the inside of the gradient magnetic field coil 12 and is configured so as to generate a high-frequency magnetic field by receiving a supply of a high-frequency pulse from the RF transmitting unit 30 (explained later), to transmit the generated high-frequency magnetic field to the patient P, and to receive a magnetic resonance signal that is released from the patient P due to the influence of the high-frequency magnetic field.

More specifically, according to the present embodiment, to take an fMRI image, the transmission/reception RF coil 13 is attached to the head of the patient P, transmits a high-frequency magnetic field to the head of the patient P, and receives a magnetic resonance signal released from the head of the patient P.

The gradient magnetic field power source 20 supplies electric current to the gradient magnetic field coil 12. The RF transmitting unit 30 transmits the high-frequency pulse corresponding to a Larmor frequency to the transmission/reception RF coil 13. The RF receiving unit 40 generates raw data by digitalizing the magnetic resonance signal that has been output from the transmission/reception RF coil 13.

The sequence controlling unit 50 exercises control while the patient P is being scanned, by driving the gradient magnetic field power source 20, the RF transmitting unit 30, and the RF receiving unit 40, based on sequence information transmitted from the computer system 80. Further, when the raw data has been transmitted from the RF receiving unit 40 as a result of the scanning of the patient P, the sequence controlling unit 50 transfers the received raw data to the computer system 80.

The "sequence information" is information that defines a procedure for performing the scanning process including, for example, the intensity of the electric power supplied from the gradient magnetic field power source 20 to the gradient magnetic field coil 12 and the timing with which the electric power is supplied, the intensity of the high-frequency pulse transmitted to the transmission/reception RF coil 13 by the RE transmitting unit 30 and the timing with which the high-frequency pulse is transmitted, and the timing with which the RE receiving unit 40 detects a Nuclear Magnetic Resonance (NMR) signal.

The bed unit 60 includes a top plate 61 on which patient P is placed. Under the control of the bed controlling unit 70 (explained later), the bed unit 60 inserts the top plate 61 having the patient P placed thereon into the hollow (i.e., an image-taking opening) inside the gradient magnetic field coil 12. Usually, the bed unit 60 is disposed so that the longitudinal direction thereof extends parallel to the central axis of the magnetostatic field magnet 11.

In this situation, while fMRI images are being taken, the patient P continuously and repeatedly performs a task for activating the motor area, the visual area, the auditory area, the language area, the sensory cortex, and the like, with intermissions of resting periods each called a "rest". For this reason, the bed unit 60 is provided with a stimulus generating device 62. The stimulus generating device 62 is a device that generates a stimulus so that the patient P is able to perform various types of tasks. For example, the stimulus generating device 62 may be a device that generates a stimulus that activates the visual area by applying light to the eyes of the patient P.

To summarize, as shown in FIG. 1, the transmission/reception RE coil 13 for performing the image taking process on the head of the patient is attached to the patient P who is placed on the top plate 61, while the stimulus generating device 62 is disposed on the line of sight of the patient P.

By driving the bed unit 60, the bed controlling unit 70 moves the top plate 61 in the longitudinal direction and in the up-and-down direction.

The computer system 80 is configured so as to, for example, exercise overall control of the MRI apparatus 100, collect data, and reconstruct images. The computer system 80 includes an interface unit 81, a data processing unit 82, a storage unit 83, an input unit 84, a display unit 85, and a controlling unit 86.

The interface unit 81 controls inputs and outputs of various types of signals that are exchanged with the sequence controlling unit 50. For example, the interface unit 81 transmits the sequence information to the sequence controlling unit 50 and receives the raw data from the sequence controlling unit 50.

The raw data that has been received by the interface unit 81 is stored into the storage unit 83, as data in a Fourier space (i.e., k-space data) with which spatial frequency information in an Slice Encode (SE) direction, a Phase Encode (PE) direction, and a Read-Out (RO) direction has been brought into correspondence by the slice selecting gradient magnetic field Gs, the phase encode gradient magnetic field Ge, and the read-out gradient magnetic field Gr that have been generated by the gradient magnetic field coil 12.

Further, the interface unit 81 transmits a bed moving request that has been input via the input unit 84 (explained later) to the bed controlling unit 70, whereas the bed controlling unit 70 drives the bed unit 60 based on the received bed moving request.

Further, the interface unit 81 transmits a stimulus generation control signal that has been transmitted from a stimulus controlling unit 86a (explained later) to the stimulus generating device 62, so that the stimulus generating device 62 generates a stimulus based on the received stimulus generation control signal. In the description of the present embodiment, an example in which stimulus generation control is exercised via the computer system 80 (described later) will be explained; however, the present embodiment is not limited to this example. Another arrangement is acceptable in which, for example, stimulus generation control is exercised via a dedicated console for operating the stimulus generating device 62.

The data processing unit 82 is a processing unit that generates image data by applying a post-processing process (i.e., a reconstructing process such as a Fourier transform) to the data in the Fourier space that has been stored as the k-space data in the storage unit 83. The data processing unit 82 includes an image generating unit 82a and a functional image generating unit 82b. More specifically, the image generating unit 82a generates a magnetic resonance image that indicates morphological information within the patient P by performing a Fourier transform on the data in the Fourier space. Further, the functional image generating unit 82b generates a magnetic resonance image (i.e., an fMRI image) that indicates brain function information of the patient P, by using the magnetic resonance image that has been generated by the image generating unit 82a. The data processing unit 82 will be explained further in detail later.

The storage unit 83 stores therein, for each of the patients including the patient P, data in the Fourier space that has been transferred from the interface unit 81, the magnetic resonance image that has been generated by the image generating unit 82a by performing a Fourier transform on the data in the Fourier space, as well as the fMRI image that has been generated by the functional image generating unit 82b by performing a statistic process on the magnetic resonance image.

The input unit 84 includes an input device for receiving inputs of various types of instructions and/or information from an operator, such as a pointing device like a mouse or a trackball, a selecting device like a mode changing switch, or a keyboard.

The display unit 85 is a monitor that is referred to by the operator. Under the control of the controlling unit 86, the display unit 85 displays various types of information such as the magnetic resonance images for the operator, and also, displays Graphical User Interface (GUI) for receiving a command from the operator via the input unit 84.

The controlling unit 86 includes a Central Processing Unit (CPU) and a memory and exercises overall control of the MRI apparatus 100. For example, the controlling unit 86 generates the sequence information based on an image-taking condition that has been input by the operator via the input unit 84 and parameters that have been set when a block setting is designed. The controlling unit 86 then performs the scanning process on the patient P, by transmitting the generated sequence information to the sequence controlling unit 50. Also, the controlling unit 86 controls the reconstructing process performed on images by the data processing unit 82. Further, the controlling unit 86 also controls screen displays realized by the display unit 85. Furthermore, the controlling unit 86 also controls the stimulus generating process performed by the stimulus generating device 62. The controlling unit 86 will be explained further in detail later.

Figure 2A:
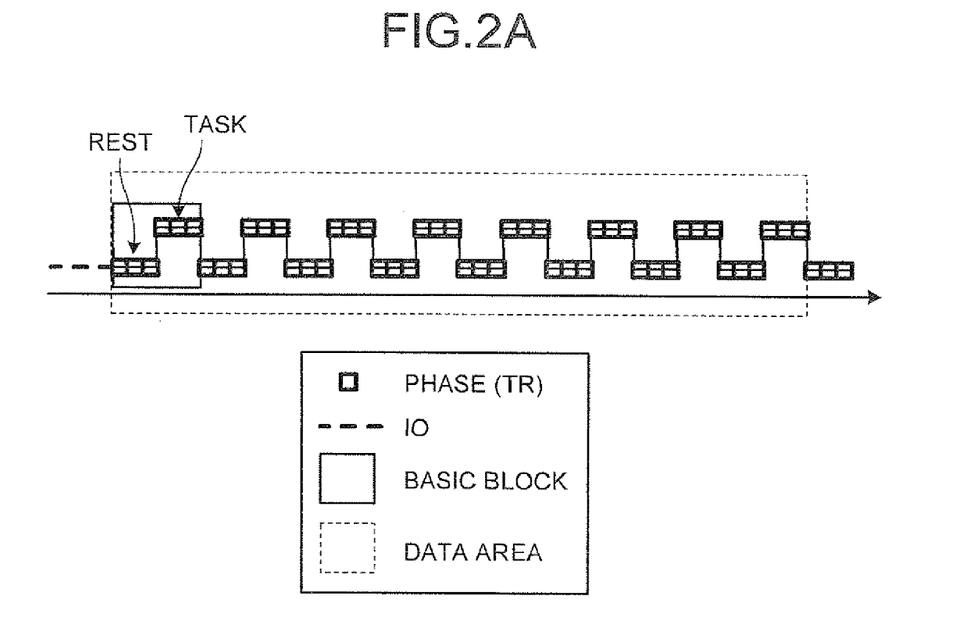
FIGS. 2A and 2B are drawings for explaining a block setting according to the embodiment.
Figure 2B:
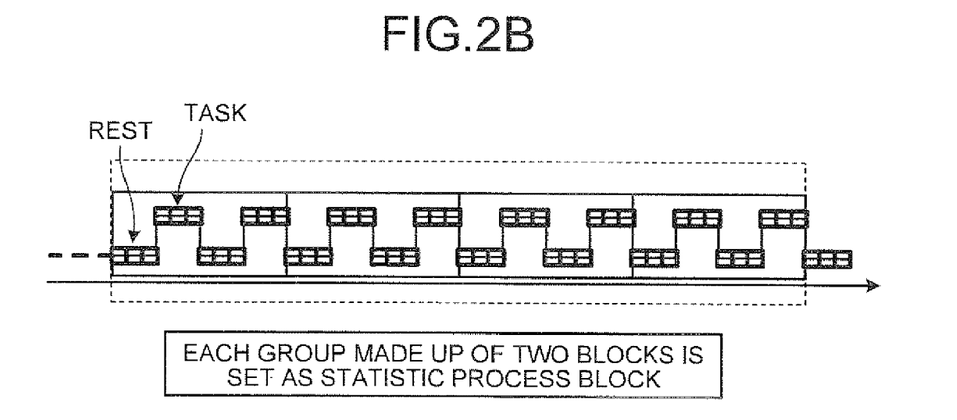
Figure 3:
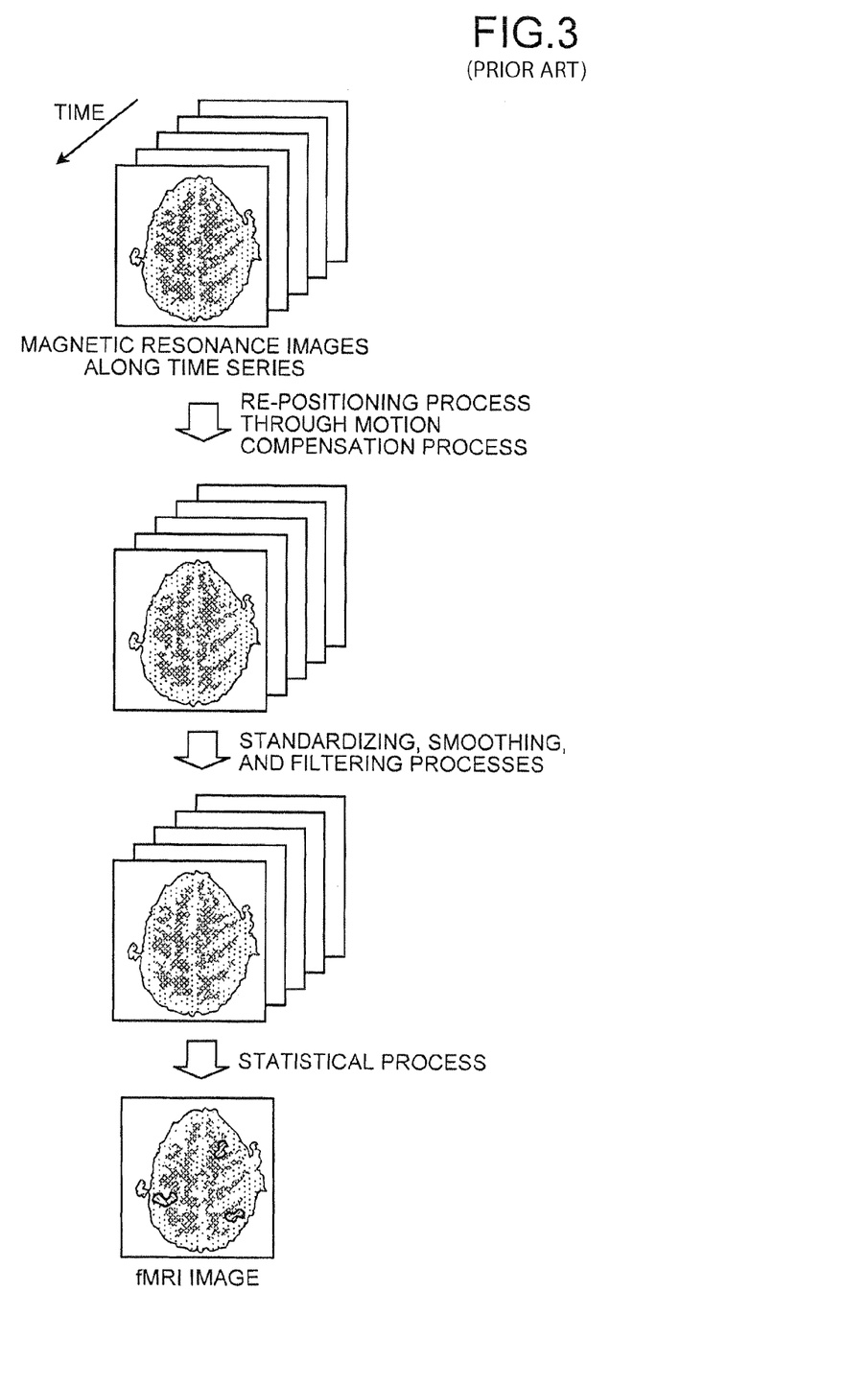
FIG. 3 is a drawing for explaining a conventional fMRI image generating process.

In this situation, the MRI apparatus 100 according to the present embodiment generates the fMRI images by using the magnetic resonance images that have been generated by collecting the magnetic resonance signal from the patient P who performs the task. A main characteristic lies in that it is possible to read the images so as to understand the manner in which a brain function activated site changes over the course of time, due to the control exercised over the data processing unit 82 by the controlling unit 86 according to the present embodiment, which is explained in detail in the following sections. This main characteristic will be explained below, with reference to FIG. 1, as well as FIGS. 2A, 2B, 3, 4, 5, 6A, and 6B. FIGS. 2A and 2B are drawings for explaining a block setting according to the present embodiment. FIG. 3 is a drawing for explaining a conventional fMRI image generating process. FIGS. 4, 5, 6A, and 61 are drawings for explaining the functional image generating unit according to the present embodiment.

As shown in FIG. 1, the controlling unit 86 according to the present embodiment includes the stimulus controlling unit

86a, an image generation controlling unit 86b, and a display controlling unit 86c. These controlling units perform various types of controlling processes, based on the image-taking condition that has been input by the operator such as a medical doctor via the input unit 84 and a block setting.

Next, the block setting will be explained once more. While fMRI images are being taken, the various types of tasks for activating the brain function are repeatedly performed with the intermissions of resting periods each called a "rest". In this situation, a setting for the lengths of the time periods during which the rests and the tasks are executed is designed with blocks that are arranged with predetermined intervals, so that a designed formation in which the blocks are arranged along the time series is obtained. Thus, the setting is called a "block setting".

More specifically, as shown in FIG. 2A, in the block setting, "phases" that are expressed by using a repetition time (hereinafter, a "TR") as a unit are used as a parameter for the setting. The block setting is established when the number of phases has been input by the operator. In other words, the operator performs the block setting process as shown in FIG. 2A by inputting the number of phases so as to indicate the quantity of rest-period blacks and task-period blocks and the number of times the rests and the tasks are repeatedly executed, together with the type of the task.

For example, in the case where the TR is set to "1000 milliseconds", in the block setting shown in FIG. 2A, the operator has established a setting in such a manner that a rest that lasts for three seconds and a task that lasts for three seconds are repeatedly executed eight times, before a rest that lasts for three seconds is executed once. The notation "IO" shown in FIG. 2A denotes an "initial offset", which is a time period that is set before the rests and the tasks start being executed so as to perform the fMRI image taking process.

First, in the block setting process according to the present embodiment, a data area used for the fMRI image generating process is set. For example, in the block setting shown in FIG. 2A, a section in which the three-second rest and the three-second task are repeatedly executed eight times is set as the data area for the magnetic resonance images used for generating the fMRI image. It should be noted that, although not shown in the drawing, in the block setting, for each of the rest time periods and the task time periods, it is also possible to set, as usage information, information indicating that all of the magnetic resonance images that are generated in the phases will be used for generating the fMRI image or information indicating that one or more of the magnetic resonance images that are generated in the phases will not be used, so that the fMRI image will be generated only from the magnetic resonance images that have been determined to be used.

Further, in the block setting process according to the present embodiment, a setting as follows will be established by the operator: the operator establishes a setting in such a manner that the plurality of magnetic resonance images that have been generated in the data area are separated into image groups each of which corresponds to a predetermined temporal phase. More specifically, the operator establishes the setting so that the plurality of magnetic resonance images that have been generated in the data area are separated into the image groups into which the magnetic resonance images are organized in such a manner that the magnetic resonance images corresponding to the rests and the tasks are sequentially contained along the time series.

Even more specifically, in the block setting process according to the present embodiment, the operator sets a basic block used for generating the fMRI image by performing a statistic process. For example, in the block setting shown in FIG. 2A, the plurality of magnetic resonance images along the time series that have been generated in the time periods that are positioned adjacent to each other along the time series (i.e., a total of six seconds) during which the rest and the task are executed one time each are set as the basic block that is used for generating the fMRI image by performing the statistic process.

Further, according to the present embodiment, as shown in FIG. 2B for example, the operator sets each group made up of two basic blocks as a statistic process block. In other words, in the block setting shown in FIG. 2B, the plurality of magnetic resonance images along the time series that have been generated in the twelve-second time period during which "rest, task, rest, task" are sequentially executed along the time series are set as the statistic process block that is used for generating one fMRI image.

As a result, the plurality of magnetic resonance images that have been generated along the time series in the time period during which the rest and the task are repeatedly executed eight times along the time series are separated into four image groups into which the magnetic resonance images are organized in such a manner that the magnetic resonance images corresponding to the rests and the tasks are sequentially contained along the time series. Accordingly, in the block setting shown in FIG. 2B, the setting has been established in such a manner that an fMRI image is generated by performing the statistic process on each of the four separate image groups.

Further, in addition to the input of the block setting explained above, the operator inputs and sets an image-taking protocol for the fMRI images (e.g., an image-taking protocol for performing the image taking process by using a Field-Echo EPI method), as the image-taking condition. The image-taking condition that has been input and set as well as the block setting are stored into the storage unit 83. When the controlling unit 86 has received, from the operator, a request indicating that an image taking process should be started, the controlling unit 86 generates the sequence information based on the image-taking condition and the block setting that have been stored in the storage unit 83 and transmits the generated sequence information to the sequence controlling unit 50. With this arrangement, the MRI apparatus 100 performs the scanning process to generate the fMRI images of the patient P.

Further, the stimulus controlling unit 86a shown in FIG. 1 controls the stimulus generating device 62 so that the stimulus generating device 62 generates a stimulus corresponding to the tasks in the block setting for each of the time periods that have been set, by transmitting a stimulus generation control signal based on the block setting stored in the storage unit 83, upon the start of the scanning process performed so as to generate the fMRI images.

Further, the image generation controlling unit 86b shown in FIG. 1 controls the image generating unit 82a and the functional image generating unit 82b that are included in the data processing unit 82 so that the image generating unit 82a and the functional image generating unit 82b generate fMRI images from the separated image groups so as to generate the plurality of fMRI images along the time series dynamic fMRI images).

More specifically, under the control of the image generation controlling unit 86b, the image generating unit 82a generates the magnetic resonance images from the data in the Fourier space that is stored in the storage unit 83 and stores the generated magnetic resonance images into the storage unit 83, while keeping the generated magnetic resonance images in correspondence with time-series information (e.g., information about the block setting that uses the TR as a unit and the usage information).

Further, under the control of the image generation controlling unit 86b, the functional image generating unit 82b reads the magnetic resonance images corresponding to the rest periods and the task-execution periods together with the time-series information, generates the fMRI images, and stores the generated fMRI images into the storage unit 83.

Next, before the fMRI image generating process performed by the functional image generating unit 82b according to the present embodiment under the control of the image generation controlling unit 86b is explained, a conventional fMRI image generating process will be particularly explained, with reference to FIG. 3. In the conventional fMRI image generating process, as shown in FIG. 3, the functional image generating unit 82b performs, at first, a re-positioning process through a motion compensation process on each of magnetic resonance images along the time series, for the purpose of reducing artifacts caused by movements of the patient P during the image taking process.

After that, as shown in FIG. 3, the functional image generating unit 82b performs, with respect to each of the magnetic resonance images on which the re-positioning process has been performed, a spatial standardizing process to standardize the image into a standard brain coordinate system, a smoothing process to improve a signal/noise (S/N) ratio, and a filtering process with respect to the temporal axis. The spatial standardizing process to standardize the images into the standard brain coordinate system is a process that is performed for the purpose of presenting each of the magnetic resonance images (i.e., the horizontally-cross-sectioned images) of the brain as projection views corresponding to three directions (i.e., a front-and-rear direction, a left-and-right direction, and an up-and-down direction) on a standardized brain map. In the past, this process was executed because the information of the areas in which the brain is activated by stimuli was not available. In these days, however, because the information of the areas in which the brain is activated by stimuli has already been collected, the spatial standardizing process to standardize the images into the standard brain coordinate system does not necessarily have to be performed.

After that, the functional image generating unit 82b generates an fMRI image in which a brain function activated site is rendered, by performing a statistical process as shown in FIG. 3, while referring to the information of the block setting that are kept in correspondence with the magnetic resonance images. For example, in the conventional fMRI image generating process, the functional image generating unit 82b generates a rest-period average image from all of the magnetic resonance images corresponding to the rest periods and generates a task-period average image from all of the magnetic resonance images corresponding to the task-execution periods. It should be noted that, however, in the case where one or more unused phases are set in the usage information explained above, the functional image generating unit 82b generates a rest-period average image from the magnetic resonance images in the phases other than the phases that have been determined to be unused during the rest periods and generates a task-period average image from the magnetic resonance images in the phases other than the phases that have been determined to be unused during the task-execution periods.

Further, the functional image generating unit 82b performs a "t-test" for determining a statistically significant difference based on a difference value and a standard error between the two population mean values with respect to the two average images and generates a "t-value image" as an fMRI original image. Further, the functional image generating unit 82b calculates a linear correlation coefficient, and also, calculates a correlation coefficient between pixel values of the fMRI original image and a reference function, so as to generate a correlation coefficient image as an fMRI image.

Figure 4:
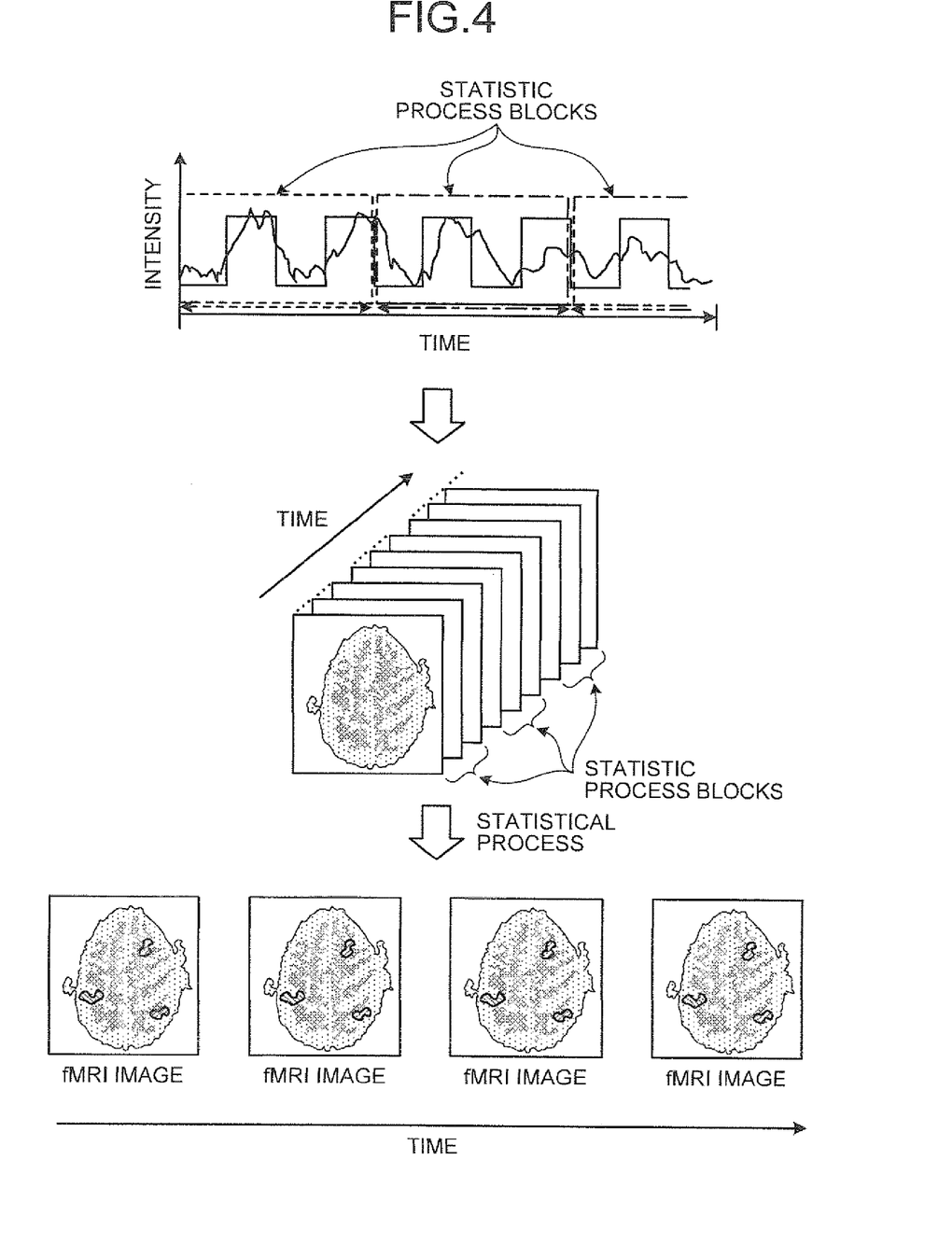
FIGS. 4, 5, 6A, and 6B are drawings for explaining a functional image generating unit according to the embodiment.

In contrast, when the functional image generating unit 82b according to the present embodiment performs the statistic process on the signal intensity of the magnetic resonance images corresponding to the rest periods and the task-execution periods that changes along the time series, because the setting has been established in such a manner that, as shown in FIG. 4, one rest period and one task period that are positioned adjacent to each other form one basic block, whereas two basic blocks that are positioned adjacent to each other form one statistic process block, the functional image generating unit 82b performs a process as follows as a statistical process, under the control of the image generation controlling unit 86b:

Under the control of the image generation controlling unit 86b based on the statistic process block that has been set, the functional image generating unit 82b according to the present embodiment generates a rest-period average image from all of the magnetic resonance images corresponding to the rest periods within the statistic process block and generates a task-period average image from all of the magnetic resonance images corresponding to the task-execution periods within the statistic process block. It should be noted that, however, in the case where one or more unused phases are set in the usage information explained above, the functional image generating unit 82b according to the present embodiment also generates a rest-period average image from the magnetic resonance images in the phases other than the phases that have been determined to be unused during the rest periods within the statistic process block and generates a task-period average image from the magnetic resonance images in the phases other than the phases that have been determined to be unused during the task-execution periods within the statistic process block.

Further, the functional image generating unit 82b according to the present embodiment performs a "t-test" with respect to the two average images in the statistic process block and generates a "t-value image" as an fMRI original image for the statistic process block. Further, the functional image generating unit 82b calculates a linear correlation coefficient, and also, calculates a correlation coefficient between pixel values of the fMRI original image and a reference function, so as to generate a correlation coefficient image as an fMRI image for the statistic process block.

As a result, the functional image generating unit 82b according to the present embodiment generates an fMRI image for each of the statistic process blocks. In other words, under the control of the image generation controlling unit 86b, the functional image generating unit 82b according to the present embodiment generates a plurality of fMRI images (i.e., dynamic fMRI images) along the time series, during one fMRI image taking process execution period, as shown in FIG. 4.

Figure 5:
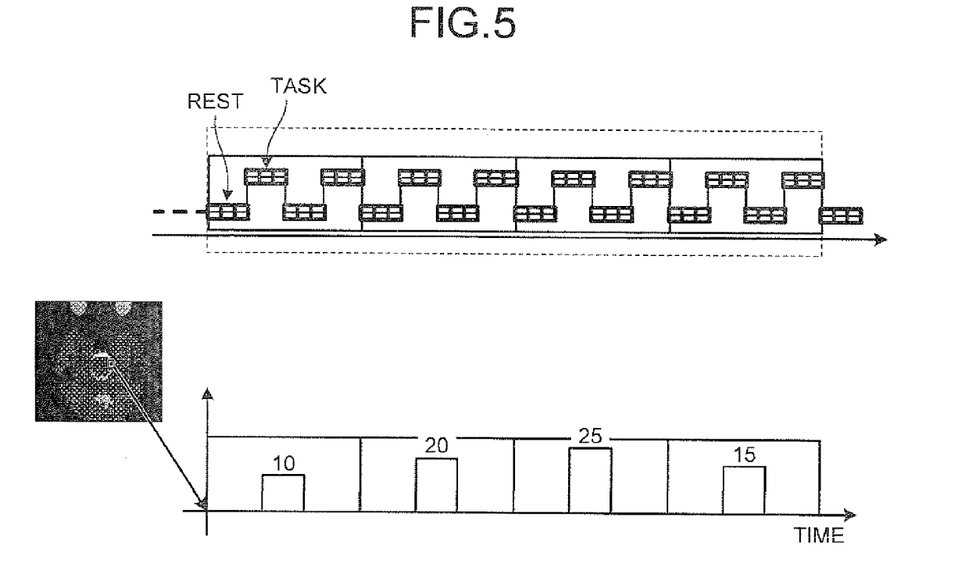

More specifically, by generating an fMRI image for each of the statistic process blocks, the functional image generating unit 82b according to the present embodiment generates, as shown in FIG. 5, dynamic fMRI images indicating that the pixel value in a Volume of Interest (VOI) or a Region of Interest (ROI) in the brain of the patient P changes as follows: "10, 20, 25, and 15".

Returning to the description of FIG. 1, the display controlling unit 86c exercises control so that the plurality of fMRI images (i.e., the dynamic fMRI images) along the time series that have been generated by the functional image generating unit 82b under the control of the image generation controlling unit 86b are displayed by the monitor included in the display unit 85.

Figure 6A:
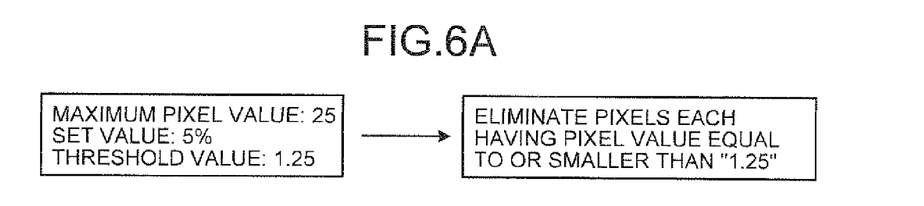

In this situation, another arrangement is acceptable in which, under the control of the image generation controlling unit 86b, the functional image generating unit 82b according to the present embodiment corrects each of the dynamic fMRI images, by eliminating, from each of the dynamic fMRI images, one or more pixels each having a pixel value that is equal to or smaller than a threshold value that has been calculated based on a maximum pixel value. For example, as shown in FIG. 6A, in the case where the maximum pixel value of the pixels that constitute the fMRI images in a statistic process block is "25", whereas a set value that has been set in advance by the operator is "5%", the image generation controlling unit 86b sets a threshold value by calculating "25× 0.05=1.25". Further, under the control of the image generation controlling unit 86b, the functional image generating unit 82b corrects the fMRI images in the statistic process block by eliminating the pixels of which the pixel value is equal to or smaller than "1.25", as shown in FIG. 6A. Further, the display controlling unit 86c exercises control so that the dynamic fMRI images that have been corrected by the functional image generating unit 82b are displayed by the monitor included in the display unit 85.

Figure 6B:
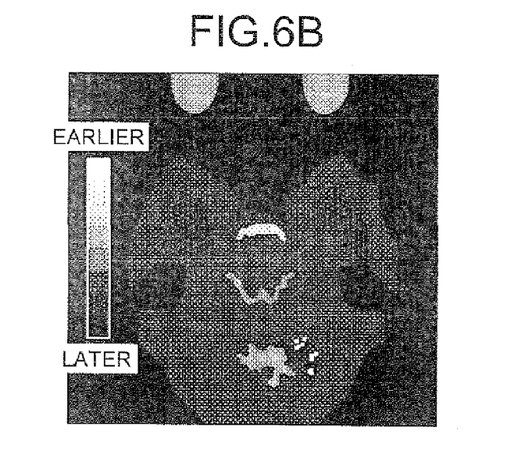

Alternatively, another arrangement is acceptable in which, under the control of the image generation controlling unit 86b, the functional image generating unit 82b according to the present embodiment generates a superimposed image in which the plurality of fMRI images along the time series are superimposed together, while the color tone of each of the fMRI images is changed along the time series, as shown in FIG. 6B. In this situation, the display controlling unit 86c exercises control so that the superimposed image that has been generated by the functional image generating unit 82b is displayed by the monitor included in the display unit 85, together with a color-tone bar that shows time-series information corresponding to each of the color tones.

Figure 7:
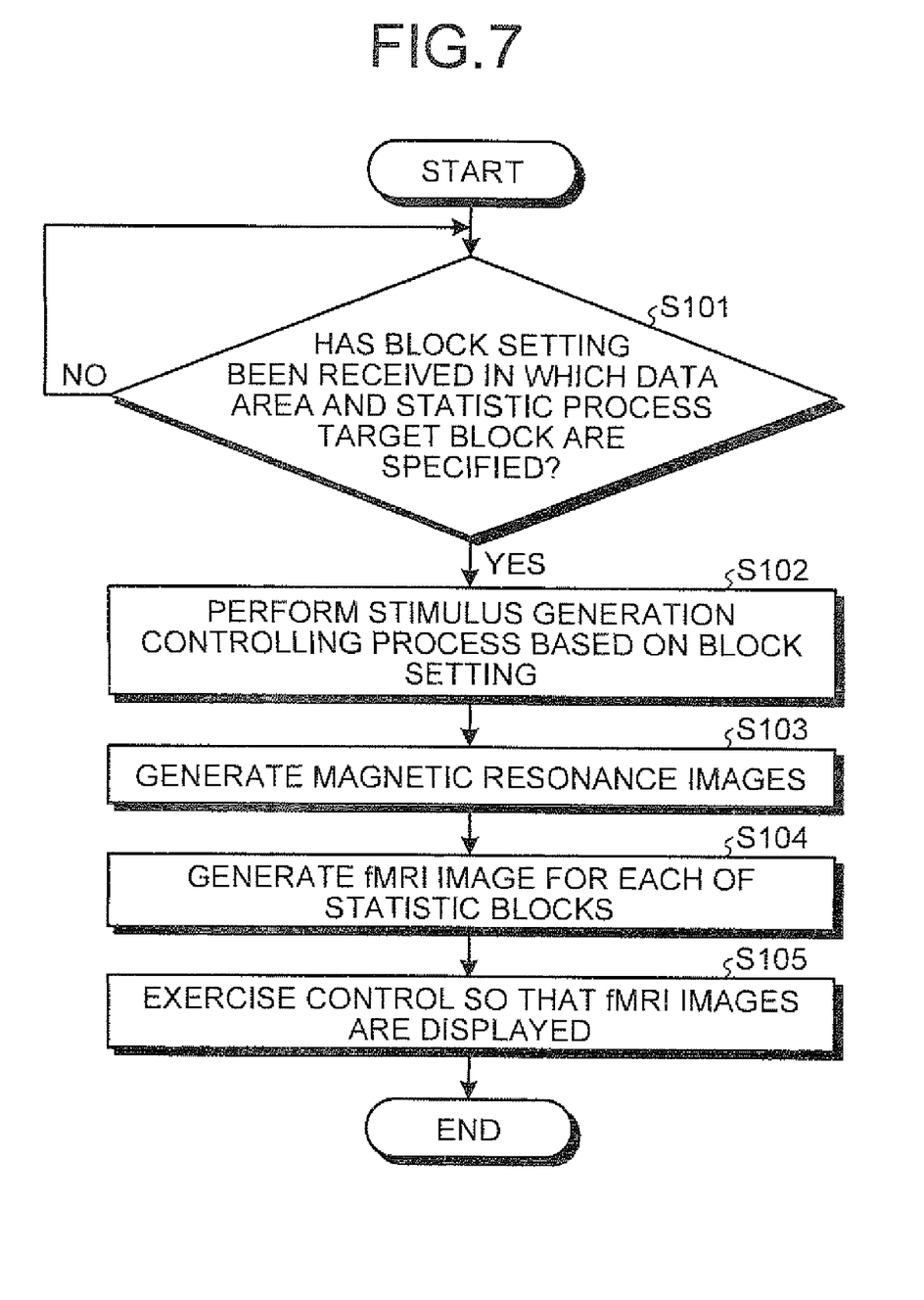
FIG. 7 is a flowchart for explaining a process performed by an MRI apparatus according to the embodiment.

Next, a process performed by the MRI apparatus 100 according to the present embodiment will be explained, with reference to FIG. 7. FIG. 7 is a flowchart for explaining the process performed by the MRI apparatus according to the present embodiment.

As shown in FIG. 7, when the MRI apparatus 100 according to the present embodiment has received a block setting in which a data area and a statistic process block are specified, together with an fMRI image-taking condition, from the operator via the input unit 84 (step S101: Yes), the stimulus controlling unit 86a performs a stimulus generation controlling process based on the block setting (step S102). In other words, the stimulus controlling unit 86a controls the stimulus generating device 62 so that the stimulus generating device 62 generates a stimulus corresponding to the tasks indicated in the block setting for each of the time periods that have been set, by transmitting a stimulus generation control signal based on the block setting.

After that, under the control of the image generation controlling unit 86b, the image generating unit 82a generates a plurality of magnetic resonance images along the time series in the data area (step S103).

Subsequently, under the control of the image generation controlling unit 86b, the functional image generating unit 82b generates an fMRI image for each of the statistic process blocks, from the magnetic resonance images (i.e., the image group) in the statistic process block (step S104). In other words, under the control of the image generation controlling unit 86b, the functional image generating unit 82b generates a plurality of fMRI images (i.e., dynamic fMRI images) along the time series, by generating an fMRI image for each of the statistic process blocks.

After that, the display controlling unit 86c exercises control so that the plurality of fMRI images along the time series that have been generated by the functional image generating unit 82b are displayed by the monitor included in the display unit 85 (step S105), and the process is thus ended.

In the case where the fMRI image correcting process explained above with reference to FIG. 6A and/or the superimposed image generating process explained above with reference to FIG. 6B are performed, these processes are performed after the process at step 5104 shown in FIG. 7 is performed, before the process at step S105 shown in FIG. 7 is performed.

As explained above, according to the present embodiment, when the statistic process blocks have been set by separating the plurality of magnetic resonance images that have been generated along the time series in the time period during which the rest and the task are repeatedly executed a plurality of times along the time series into the image groups into which the magnetic resonance images are organized while one rest period and one task-execution period that are positioned adjacent to each other along the time series form one basic block, the image generation controlling unit 86b controls the functional image generating unit 82b so that the functional image generating unit 82b generates an fMRI image for each of the statistic process blocks by performing, for each of the statistic process blocks, the statistic process on the plurality of magnetic resonance images along the time series that have been generated by the image generating unit 82a. Further, the display controlling unit 86c exercises control so that the fMRI images corresponding to the statistic process blocks that have been generated by the functional image generating unit 82b are displayed by the monitor included in the display unit 85.

With these arrangements according to the present embodiment, even in the case where it takes a certain period of time for the brain to be activated after being stimulated, it is possible to generate and display the plurality of fMRI images along the time series in any single time period during which the rest and the task are repeatedly executed a plurality of times along the time series. Thus, as explained above as a main characteristic, it is possible to read the images so as to understand the manner in which the brain function activated site changes over the course of time.

Figure 8A:
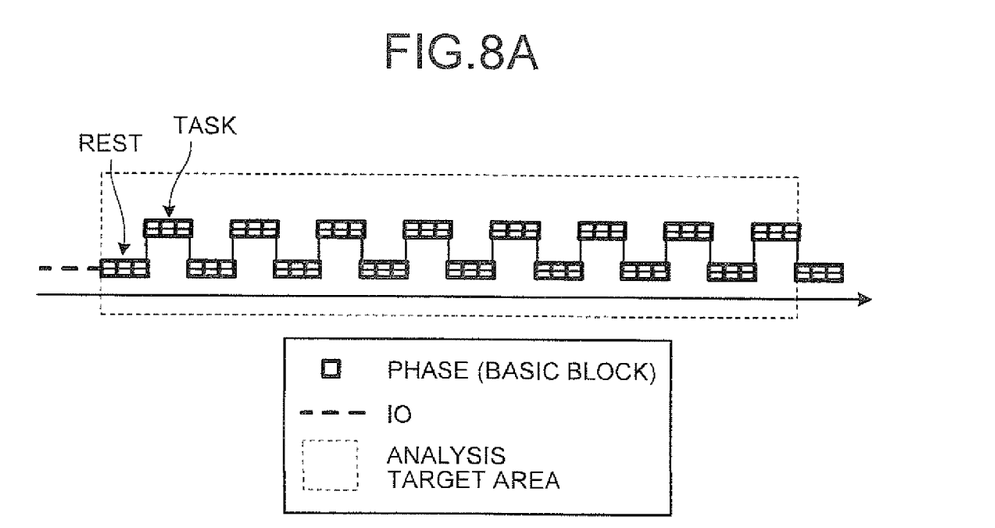
Figure 8B:
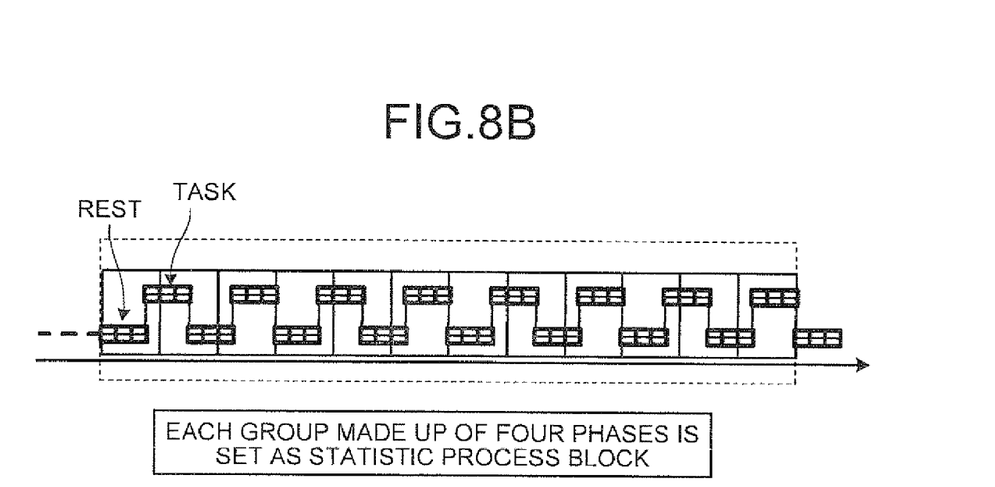
Figure 9A:
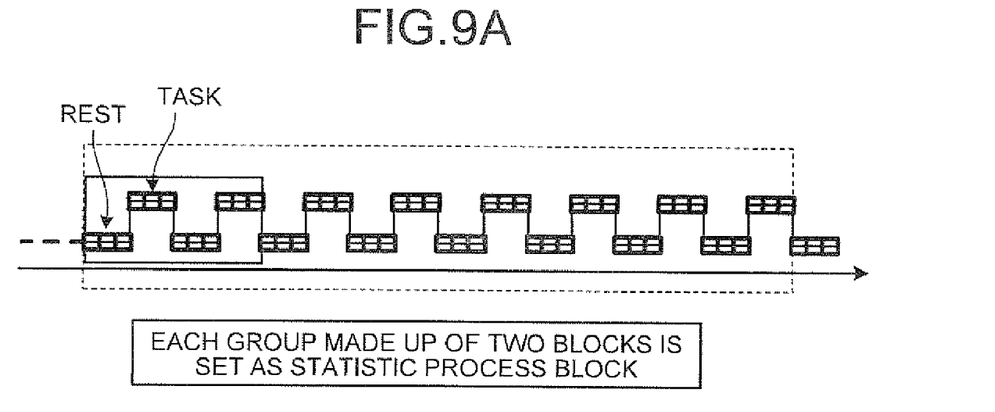
FIGS. 9A and 9B are drawing for explaining a second modification example.
Figure 9B:
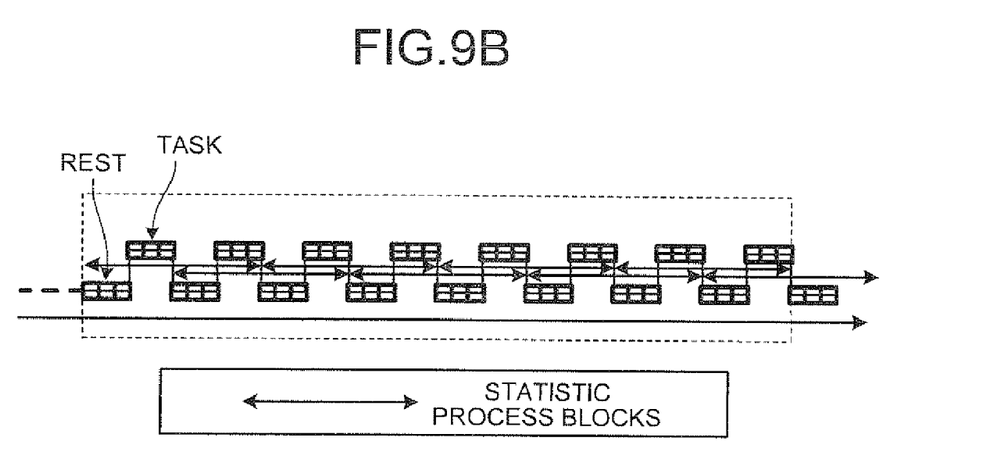
Figure 10:
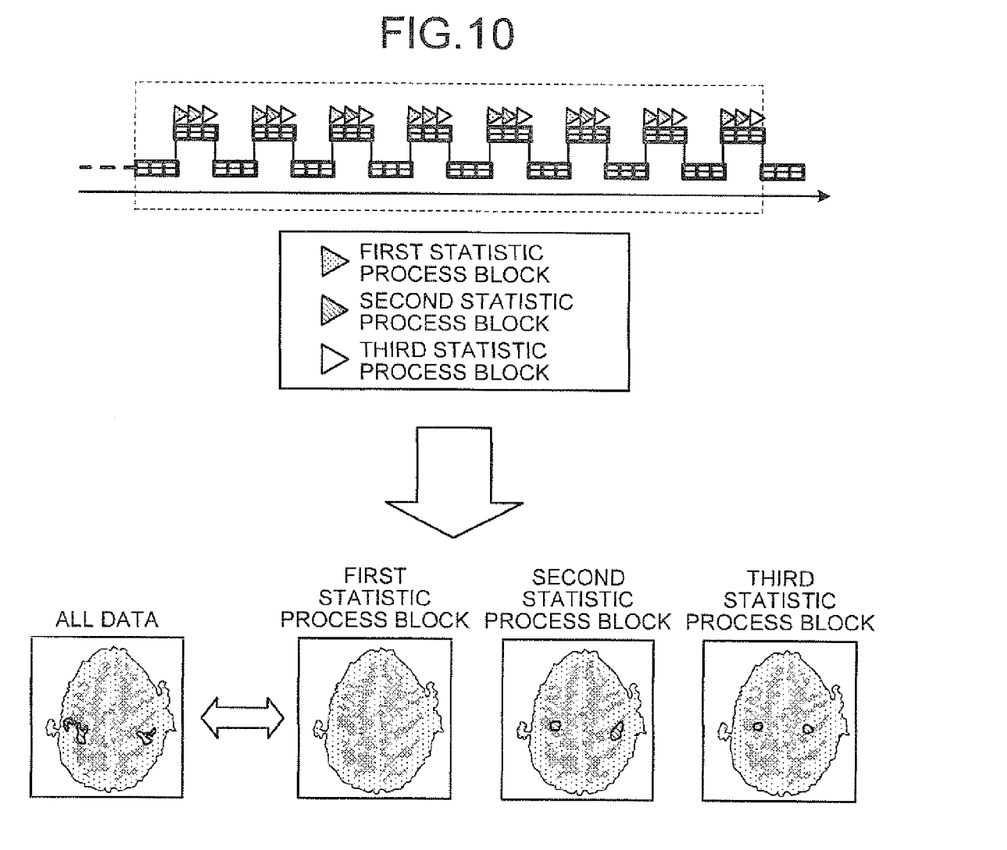
FIG. 10 is a drawing for explaining a third modification example.

As explained above, while using the block setting, the MRI apparatus 100 according to the present embodiment generates the dynamic fMRI images by separating the plurality of magnetic resonance images that have been generated in the data area into the image groups into which the magnetic resonance images are organized in such a manner that the magnetic resonance images corresponding to the rest periods and the task-execution periods are sequentially contained along the time series. The method used for setting the separation of the image groups, however, is not limited to the separation setting method explained with reference to FIGS. 2A and 2B. Thus, in the following sections, three modification examples of the separation setting method of the image groups will be explained, with reference to FIGS. 8A, 8B, 9A, 9B, and 10. FIGS. 8A and 8B are drawings for explaining a first modification example. FIGS. 9A and 9B are drawing for explaining a second modification example. FIG. 10 is a drawing for explaining a third modification example.

According to the first modification example, as shown in FIG. 8A, a basic block is set as "the phase that uses TR as a unit", which is the parameter used in the block setting process. Further, according to the first modification example, as shown in FIG. 8B as en example, each group made up of four phases is set as a statistic process block. In other words, in the block setting shown in FIG. 8B, the statistic process block is set while the number of phases is adjusted in such a manner that a magnetic resonance image generated during a rest period and a magnetic resonance image generated during a task-execution period are always sequentially contained in the statistic process block.

As a result, according to the first modification example, it is possible to separate the plurality of magnetic resonance images that have been generated in the data area with a finer granularity than in the example of the separation setting method of the image groups explained above in the description of the exemplary embodiments. Thus, it is possible to generate and display dynamic fMRI images having a high temporal resolution. Consequently, it is possible to read the images so as to understand, further in detail, the manner in which the brain function activated site that changes over the course of time.

In the second modification example, the magnetic resonance images that have been generated in the time periods that are positioned adjacent to each other along the time series during which the rest and the task are executed one time each are set as a basic block, like in the example shown in FIG. 2A. Further, according to the second modification example, each group made up of two basic blocks is set as a statistic process block as shown in FIG. 9A, like in the example shown in FIG. 2B.

According to the second modification example, however, each of the statistic process blocks is set in an overlapping manner, as shown in FIG. 9B, so that one basic block is shared between a preceding statistic process block and a following statistic process block. In other words, according to the second modification example, the plurality of magnetic resonance images that have been generated in the data area are separated into the image groups into which the magnetic resonance images are organized in such a manner that the magnetic resonance images generated during the rest periods and the task-execution periods are sequentially contained along the time series and are contained in the overlapping manner.

As a result, according to the second modification example, each of the plurality of fMRI images along the time series is generated from the overlapping magnetic resonance images. Thus, it is possible to ensure that the brain activated area rendered in each of the fMRI images is, without fail, information reflecting the magnetic resonance image serving as a generation source of the fMRI image in the preceding position on the temporal axis. Consequently, it is possible to read the images so as to understand, without fail, the manner in which the brain function activated site changes over the course of time.

In the third modification example, among the plurality of magnetic resonance images that have been generated in the data area, a plurality of magnetic resonance images corresponding to the task-execution periods are separated into a plurality of image groups according to elapsed time periods since the start of the execution of the task. In this situation, under the control of the image generation controlling unit 86b, the functional image generating unit 82b generates a plurality of fMRI images along the time series, by using the plurality of image groups obtained by separating the plurality of magnetic resonance images corresponding to the task-execution periods according to the elapsed time periods since the start of the execution of the task.

For example, according to the third modification example, each of the task-execution periods is divided into three sections that respectively correspond to a first statistic process block, a second statistic process block, and a third statistic process block, as shown in FIG. 10. For example, in the case where the task-execution period is 30 seconds, the first statistic process block corresponds to a time period from the start of the task to the point in time at which 10 seconds have elapsed since the start of the task; the second statistic process block corresponds to a time period from the point in time at which 10 seconds have elapsed since the start of the task, to the point in time at which 20 seconds have elapsed since the start of the task; and the third statistic process block corresponds to a time period from the point in time at which 20 seconds have elapsed since the start of the task, to the point in time at which 30 seconds have elapsed since the start of the task.

Further, as shown in FIG. 10, the functional image generating unit 82b performs a statistic process on all of the magnetic resonance images in the first statistic process block corresponding to the task-execution period repeated eight times and on the plurality of magnetic resonance images corresponding to the rest period repeated eight times (e.g., the plurality of magnetic resonance images corresponding to the time periods each of which lasts from the start of the rest to the point in time at which 10 seconds have elapsed since the start of the rest. As a result, the functional image generating unit 82b generates an fMRI image for the first statistic process block, as shown in FIG. 10.

Further, as shown in FIG. 10, the functional image generating unit 82b performs a statistic process on all of the magnetic resonance images in the second statistic process block corresponding to the task-execution period repeated eight times and on the plurality of magnetic resonance images corresponding to the rest period repeated eight times (e.g., the plurality of magnetic resonance images corresponding to the time periods each of which lasts from the point in time at which 10 seconds have elapsed since the start of the rest, to the point in time at which 20 seconds have elapsed since the start of the rest). As a result, the functional image generating unit 82b generates an fMRI image for the second statistic process block, as shown in FIG. 10.

Further, as shown in FIG. 10, the functional image generating unit 82b performs a statistic process on all of the magnetic resonance images in the third statistic process block corresponding to the task-execution period repeated eight times and on the plurality of magnetic resonance images corresponding to the rest period repeated eight times (e.g., the plurality of magnetic resonance images corresponding to the time periods each of which lasts from the point in time at which 20 seconds have elapsed since the start of the rest, to the point in time at which 30 seconds have elapsed since the start of the rest). As a result, the functional image generating unit 82b generates an fMRI image for the third statistic process block, as shown in FIG. 10.

As shown in FIG. 10, for example, within the fMRI image that has been generated from the magnetic resonance images corresponding to all of the task-execution periods, all the areas that have been activated due to the execution of the task are rendered. In contrast, according to the third modification example, it is possible to generate and display an fMRI image that renders, in detail and along the time series, the manner in which the brain activated area changes during the task-execution periods. As a result, according to the third modification example, it is possible to read the images so as to understand, in detail, the manner in which the brain function activated site changes over the course of time during the task-execution periods.

In the sections above, the example is explained in which the plurality of magnetic resonance images corresponding to the rest periods that are used as a target of the statistic process are set in such a manner that the magnetic resonance images correspond to the time periods of the statistic process blocks corresponding to the task-execution periods; however, the plurality of magnetic resonance images corresponding to the rest periods that are used as a target of the statistic process according to the third modification example may be arbitrarily set, as long as the number of magnetic resonance images is the same as the number of magnetic resonance images in each of the statistic process blocks.

In the description of the exemplary embodiments and the modification examples above, the example has been explained in which, after the generation of the stimulus based on the block setting has finished, the magnetic resonance images in the data area are generated, so that the dynamic fMRI image for each of the statistic process blocks is generated and displayed. However, the exemplary embodiments and the modification examples are not limited to this example; another arrangement is acceptable in which, in a time period during which the stimuli generation process is performed based on the block setting, a dynamic fMRI image is generated and displayed one by one, every time magnetic resonance images are generated for a statistic process block. In other words, the dynamic fMRI images may be generated and displayed by performing a post-processing process. Alternatively, the dynamic fMRI images may be generated and displayed in a real-time manner.

More specifically, in the case where the dynamic fMRI images are generated and displayed in a real-time manner, after starting a stimulus generating process, the MRI apparatus 100 sequentially generates magnetic resonance images based on the data in the Fourier space that has been collected. After that, every time a group of magnetic resonance images for a statistic process block has been generated, the MRI apparatus 100 generates an fMRI image and causes the generated fMRI image to be displayed one by one.

Further, in the description of the exemplary embodiments and the modification examples above, the example has been explained in which the image groups for generating the dynamic fMRI images are set by setting the statistic process blocks while using the magnetic resonance images as the target; however, the exemplary embodiments and the modification examples are also applicable to a situation in which the image groups for generating the dynamic fMRI images are set by setting the statistic process blocks while using the data in the Fourier space used for generating the magnetic resonance images as the target.

Further, in the description of the exemplary embodiments and the modification examples above, the example has been explained in which the MRI apparatus 100 generates and displays the dynamic fMRI images; however, according to the exemplary embodiments and the modification examples, another arrangement is acceptable in which an image processing apparatus that is provided independently from the MRI apparatus 100 generates and displays the dynamic fMRI images by using the magnetic resonance images that have been generated by the MRI apparatus 100.

Furthermore, the images that are generated and displayed by the image processing apparatus described above do not necessarily have to be dynamic fMRI images. For example, image processing apparatus is applicable to an example in which a perfusion image indicating a dynamic state of blood streams is generated from a plurality of magnetic resonance images that have been generated along the time series. Further, the image processing apparatus is also applicable to an example in which a perfusion image is generated from a plurality of X-ray Computed Tomography (CT) images or the like that have been generated along the time series.

In other words, the image processing apparatus described above generates and displays a plurality of perfusion images along the time series by separating the plurality of medical images that have been generated along the time series into image groups each of which corresponds to a predetermined temporal phase and by performing a statistic process on each of the image groups resulting from the separation.

As a result, it is possible to read the images so as to understand the manner in which the dynamic state of the blood streams changes over the course of time.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
an image generating unit configured to generate magnetic resonance images by acquiring magnetic resonance signals from an examined subject who repeatedly executes a task with an intermission resting period;
a functional image generating unit configured to generate a functional-diagnosis-purpose magnetic resonance image from said magnetic resonance images;
an image generation controlling unit configured to control the functional image generating unit to generate a plurality of functional images along a time series by separating a plurality of magnetic resonance images that have been generated along the time series during a collecting period into image groups, each of which corresponds to a predetermined temporal phase and by performing a statistical process on each of the separated image groups, the collecting period being configured so that the resting period and a task-execution period during which the task is executed are repeated therein a plurality of times along the time series; and
a display controlling unit configured to cause the plurality of functional images along the time series that have been generated under control of the image generation controlling unit to be displayed by a display unit.

2. The magnetic resonance imaging apparatus according to claim 1, wherein:
the image generation controlling unit controls the functional image generating unit to generate the plurality of functional images along the time series by separating the plurality of magnetic resonance images that have been generated along the time series during the collecting period into image groups into which the magnetic resonance images are organized in such a manner that the magnetic resonance images corresponding to the resting periods and the task-execution periods are sequentially contained along the time series.

3. The magnetic resonance imaging apparatus according to claim 2, wherein:

the image generation controlling unit controls the functional image generating unit to generate the plurality of functional images along the time series by separating the plurality of magnetic resonance images that have been generated along the time series during the collecting period into image groups that are obtained by using the resting period and the task-execution period that are positioned adjacent to each other along the time series as a basic unit.

4. The magnetic resonance imaging apparatus according to claim 2, wherein:

the image generation controlling unit controls the functional image generating unit to generate the plurality of functional images along the time series by separating the plurality of magnetic resonance images that have been generated along the time series during the collecting period into image groups that are obtained by using a temporal phase unit employed for setting the resting periods and the task-execution periods as a basic unit.

5. The magnetic resonance imaging apparatus according to claim 2, wherein:

the image generation controlling unit controls the functional image generating unit to generate the plurality of functional images along the time series by separating the plurality of magnetic resonance images that have been generated along the time series during the collecting period into image groups into which the magnetic resonance images are organized in such a manner that the resonance magnetic resonance images corresponding to the resting periods and the task-execution periods are sequentially contained along the time series and are contained in an overlapping manner.

6. The magnetic resonance imaging apparatus according to claim 2, wherein:

the image generation controlling unit controls the functional image generating unit to generate a superimposed image in which the plurality of functional images along the time series are superimposed together, while a color tone of each of the functional images is changed along the time series, and the display controlling unit exercises control so that the superimposed image that has been generated under control of the image generation controlling unit is displayed by the display unit.

7. The magnetic resonance imaging apparatus according to claim 6, wherein:

the image generation controlling unit controls the functional image generating unit to correct each of the plurality of functional images along the time series by eliminating, from each of the plurality of functional images along the time series, one or more pixels each having a pixel value that is equal to or smaller than a threshold value that has been calculated based on a maximum pixel value.

8. The magnetic resonance imaging apparatus according to claim 2, wherein:

the image generation controlling unit controls the functional image generating unit to correct each of the plurality of functional images along the time series by eliminating, from each of the plurality of functional images along the time series, one or more pixels each having a pixel value that is equal to or smaller than a threshold value that has been calculated based on a maximum pixel value.

9. The magnetic resonance imaging apparatus according to claim 1, wherein:

the image generation controlling unit controls the functional image generating unit to generate the plurality of functional images along the time series by separating a plurality of magnetic resonance images corresponding to the task-execution periods that are among the plurality of magnetic resonance images that have been generated along the time series during the collecting period into a plurality of image groups, according to an elapsed time period since a start of execution of the task.

10. The magnetic resonance imaging apparatus according to claim 9, wherein:

the image generation controlling unit controls the functional image generating unit to generate a superimposed image in which the plurality of functional images along the time series are superimposed together, while a color tone of each of the functional images is changed along the time series, and the display controlling unit exercises control so that the superimposed image that has been generated under control of the image generation controlling unit is displayed by the display unit.

11. The magnetic resonance imaging apparatus according to claim 10, wherein:

the image generation controlling unit controls the functional image generating unit to correct each of the plurality of functional images along the time series by eliminating, from each of the plurality of functional images along the time series, one or more pixels each having a pixel value that is equal to or smaller than a threshold value that has been calculated based on a maximum pixel value.

12. The magnetic resonance imaging apparatus according to claim 9, wherein:

the image generation controlling unit controls the functional image generating unit to correct each of the plurality of functional images along the time series by eliminating, from each of the plurality of functional images along the time series, one or more pixels each having a pixel value that is equal to or smaller than a threshold value that has been calculated based on a maximum pixel value.

13. The magnetic resonance imaging apparatus according to claim 1, wherein:

the image generation controlling unit controls the functional image generating unit to generate a superimposed image in which the plurality of functional images along the time series are superimposed together, while a color tone of each of the functional images is changed along the time series, and the display controlling unit exercises control so that the superimposed image that has been generated under control of the image generation controlling unit is displayed by the display unit.

14. The magnetic resonance imaging apparatus according to claim 13, wherein:

the image generation controlling unit controls the functional image generating unit to correct each of the plurality of functional images along the time series by eliminating, from each of the plurality of functional images along the time series, one or more pixels each having a pixel value that is equal to or smaller than a threshold value that has been calculated based on a maximum pixel value.

15. The magnetic resonance imaging apparatus according to claim 1, wherein:

the image generation controlling unit controls the functional image generating unit to correct each of the plurality of functional images along the time series by eliminating, from each of the plurality of functional images along the time series, one or more pixels each having a pixel value that is equal to or smaller than a threshold value that has been calculated based on a maximum pixel value.

16. An image processing apparatus comprising:
a functional image generating unit that generates a functional image from an examined subject who repeatedly executes a task with an intermission of a resting period;
an image generation controlling unit that controls the functional image generating unit to generate a plurality of functional images along a time series by separating a plurality of magnetic resonance images that have been generated along the time series during a collecting period into image groups, each of which corresponds to a predetermined temporal phase and by performing a statistical process on each of the separated image groups, the collecting period being configured so that the resting period and a task-execution period during which the task is executed are repeated therein a plurality of times along the time series; and
a display controlling unit that exercises control so that the plurality of functional images along the time series that have been generated under control of the image generation controlling unit are displayed by a display unit.

17. An image processing apparatus comprising:
a functional image generating unit that generates a functional image, which is a functional-diagnosis-purpose medical image, from a plurality of medical images that have been generated along a time series;
an image generation controlling unit that controls the functional image generating unit to generate a plurality of functional images along the time series by separating the plurality of medical images that have been generated along the time series into image groups, each of which corresponds to a predetermined temporal phase and by performing a statistic process on each of the image groups resulting from the separation; and
a display controlling unit that exercises control so that the plurality of functional images along the time series that have been generated under control of the image generation controlling unit are displayed by a display unit.

18. An image processing method comprising:
generating a functional image, which is a functional-diagnosis-purpose magnetic resonance image, from a magnetic resonance image that has been generated by collecting a magnetic resonance signal from an examined subject who repeatedly executes a task with an intermission of a resting period;
controlling the functional image generating unit to generate a plurality of functional images along a time series by separating a plurality of magnetic resonance images that have been generated along the time series during a collecting period into image groups, each of which corresponds to a predetermined temporal phase and by performing a statistic process on each of the image groups resulting from the separation, the collecting period being configured so that the resting period and a task-execution period during which the task is executed are repeated therein a plurality of times along the time series; and
exercising control so that the plurality of functional images along the time series that have been generated under control of the image generation controlling unit are displayed by a display unit.

19. An image processing method comprising:
generating a functional image, which is a functional-diagnosis-purpose medical image, from a plurality of medical images that have been generated along a time series;
controlling the functional image generating unit to generate a plurality of functional images along the time series by separating the plurality of medical images that have been generated along the time series into image groups, each of which corresponds to a predetermined temporal phase and by performing a statistic process on each of the image groups resulting from the separation; and
exercising control so that the plurality of functional images along the time series that have been generated under control of the image generation controlling unit are displayed by a display unit.

* * * * *